United States Patent [19]

Grimsrud

[11] 4,190,536
[45] Feb. 26, 1980

[54] PERISTALTIC PUMPING MEANS FOR BLOOD DIALYSIS

[75] Inventor: Lars Grimsrud, Salmon, Id.

[73] Assignee: A/S Nycotron, Drammen, Norway

[21] Appl. No.: 880,156

[22] Filed: Feb. 22, 1978

[30] Foreign Application Priority Data

Feb. 23, 1977 [NO] Norway ........................ 770605

[51] Int. Cl.² .............................................. B01D 31/00
[52] U.S. Cl. .................................. 210/93; 210/321 B; 210/416 M
[58] Field of Search ............ 210/87, 40, 96 M, 321 B, 210/22 A, 416 M, 93, 85; 137/99

[56] References Cited

U.S. PATENT DOCUMENTS

| 3,939,069 | 2/1976 | Granger et al. | 210/22 A |
| 3,946,731 | 3/1976 | Lichtenstein | 210/87 X |
| 4,021,341 | 3/1977 | Cosentino et al. | 210/87 |
| 4,037,616 | 9/1977 | Pinkerton | 137/99 |

Primary Examiner—Frank A. Spear, Jr.
Attorney, Agent, or Firm—Watson, Cole, Grindle & Watson

[57] ABSTRACT

A dialysis apparatus for regulated blood dialysis includes a dialyser having flow passages for blood and dialysate, respectfully, separated by semipermeable barriers for transferring liquid from the blood to the dialysate, the blood and dialysate being driven through their respective flow passages by individually associated peristaltic pumps mounted on a common shaft and having the same pumping capacity and being respectively disposed on the inlet and outlet sides of the flow passage for dialysate through the dialyser. A tap outlet is provided between the pumps in communication with the passage. The liquid amount tapped off the tap outlet must therefore be equal to the amount of ultrafiltrate extracted from the blood, and thus the latter amount may readily be gauged and supervised.

2 Claims, 4 Drawing Figures

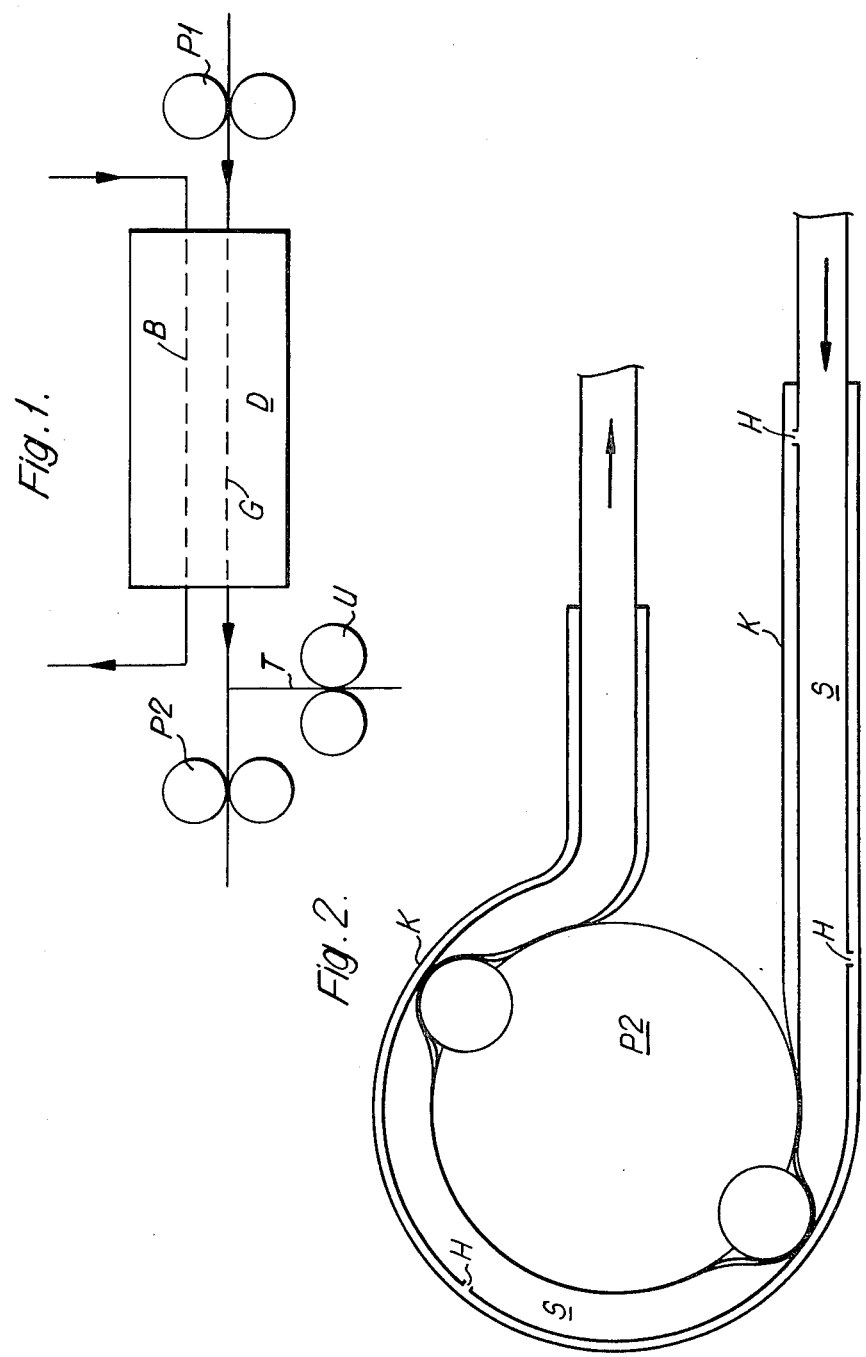

PERISTALTIC PUMPING MEANS FOR BLOOD DIALYSIS

This invention relates generally to a dialysis apparatus for regulated blood dialysis, and comprises a dialyzer with flow passages for blood and dialysate, respectively, separated by semipermeable barriers for transferring liquid from the blood to the dialysate, the blood and dialysate being driven through their respective flow passages by means of individually associated pumping means.

Dialysis apparatus of this type usually serve as artificial kidneys for extracting waste material from the blood of a patient, and being dissolved in the liquid which is transferred to the dialysate through said semipermeable barriers. Such barriers may be designed in many ways, e.g., as semipermeable membranes between dialyser departments filled with blood and dialysate, respectively, or as thin-walled tubes, through the inside of which dialysate is circulated and the outside of which is irrigated by blood.

With dialysis of the blood of a patient in this manner, it has been recently found that it is conclusive of the efficiency of the dialyzing process and the general welfare of the patient, that the so-called ultrafiltrate which is extracted from the blood of the patient, be subject to continuous supervision and suitable regulation. Such gauging of the amount of liquid extracted from the patient's blood is in principle quite easy to perform in dialysis apparatus with recirculated dialysate, and the necessary measurement may for example be performed by continuously removing any excess liquid added to the recirculating liquid volume in the dialysate circuit which is assumed completely filled with liquid. If no leakage is present, the removed liquid volume will necessarily be equal to the volume of the liquid supplied to the dialysate circuit from the dialyzed blood of the patient, and this volume of liquid will be a direct measure of the amount of ultrafiltrate extracted from the blood. If, however, in fact leakage is present or gases dissolved in the dialysate are released under influence of the subpressure which is required to maintain the desired extraction of ultrafiltrate, the tapped amount of liquid is apt to give an erroneous indication of the ultrafiltrate volume in question, as part of the tapped liquid may have been replaced by air or gas in the circulation circuit rather than by ultrafiltrate.

U.S. patent application Ser. No. 810,726 discloses now U.S. Pat. No. 4,132,644 weighing of the liquid content of a closed circulation circuit for dialysate, in order that the amount of ultrafiltrate which has been added to this circuit in the course of a dialysis treatment may be determined at any time. This procedure has the advantage in that it is not influenced by the varying content of gas or air in the circulation circuit, although it requires more complex gauging and regulation apparatus than the simple determination of tapped liquid amount by volume measurement, as described above.

In view of the state of art in this field, as discussed above, it is an object of the present invention to provide a dialysis apparatus which allows measurement and regulation of the extracted amount of ultrafiltrate from the blood of a patient even if such apparatus does not operate with recirculating dialysate, but the dialysate supplied to the dialyser is discharged through an outlet conduit upon one single flow passage through the apparatus, and at the same time under all operating conditions secures a more welldefined determination of the extracted amount of ultrafiltrate, which to a lesser extent than before is influenced by various operational irregularities in the apparatus.

In a dialysis apparatus of the initially indicated type, the above objects are achieved according to the invention due to the special features that the pumping means for the dialysate comprises two pump units having the same pumping capacity and are disposed on the inlet and the outlet sides, respectively, of the flow passage for dialysate through the dialyser, a tap outlet connected with means for gauging the amoung of tapped liquid being arranged in communication with the flow passage between the two pump units.

As the two pump units have the same pumping capacity, the dialysate will necessarily be removed from the outlet of the dialyser at the same rate as such liquid is supplied to the inlet of the dialysate passage through the dialyser. Thus, the amount of liquid which is tapped off through the tap outlet between the two pump units, must obviously correspond to the amount of ultrafiltrate which is extracted from the blood in the dialyser between the pump units.

Thus, it is only the operational conditions prevailing between the pump units which are of importance for the amount of liquid which is tapped off and measured, and possible irregularities, e.g., leakages, in the other components of the dialysate circuit, e.g., heat exchanger, dialysate concentration gauge, valve means, dialysate cleansing means, will not influence the measurement, without regard to the flow circuit being open or closed.

The two pump units preferably comprise a pair of peristaltic pumps on a common drive shaft, one of the pump units being connected between a dialysate source and the inlet of the flow passage for dialysate through the dialyser, and the other pump being connected between the outlet of the flow passage and a dialysate discharge conduit. This arrangement will function equally well whether the liquid in the discharge conduit is transferred back to the dialysate source, or is directed to a drain without further use.

Further, the tap outlet may according to the invention be provided with means, e.g., an adjustable pump, for automatic regulation of the tapped amount of liquid and thereby the internal pressure in the flow passage for dialysate through the dialyser. As the amount of ultrafiltrate which can be extracted from the blood in a dialyser, is strongly dependent of the prevailing subpressure in the flow passage of the dialysate, the removed amount of ultrafiltrate may in this way be automatically regulated in addition to being measured and supervised.

For further illustration of the apparatus according to the present invention, preferred embodiments will now be described with reference to the accompanying drawings, wherein:

FIG. 1 schematically shows a first embodiment of the apparatus according to the invention;

FIG. 2 shows a detail of the first embodiment; and

Figure 3A:
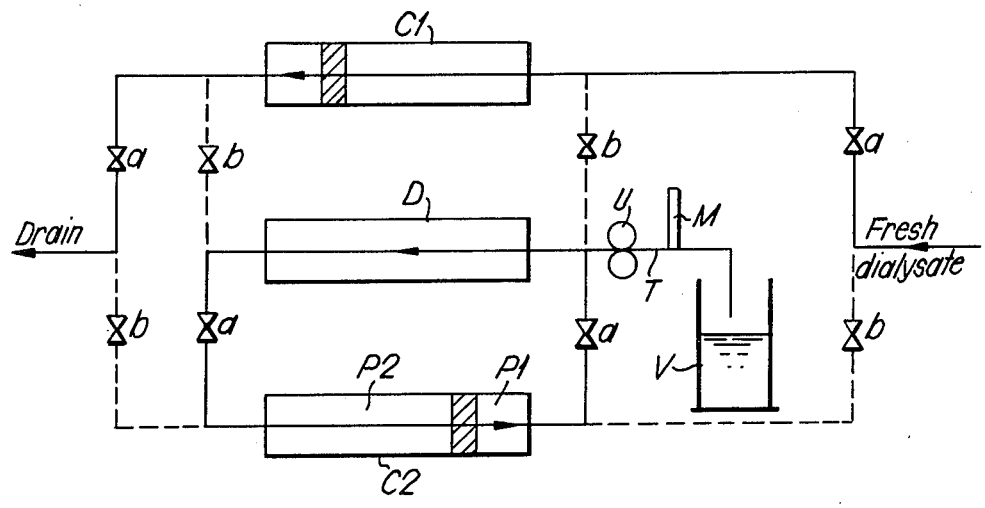
FIGS. 3a and 3b show another embodiment of the present apparatus.

Referring now to the drawings, FIG. 1 shows a dialyser D with a through-flow passage B for blood and a through-flow passage G for dialysate, the passages being separated by a semipermeable barrier (not shown) which allows extraction of a liquid solution containing poisonous and waste materials from the blood and transfer of the solution to the dialysate in the flow passage G, the dialyser thus serving as an artificial kidney.

Pumping means P1, P2 is provided to drive dialysate through the flow passage G of the dialysate, and comprises a pump unit P1 on the inlet side of the dialyser and a pump unit P2 on its outlet side. These pump units comprise a pair of identical peristaltic pumps on a common drive shaft. The pump units P1 and P2 are disposed one on each side of the dialyser D, a tap outlet T from the dialysate flow passage being provided between the dialyser and one of the pump units.

For appropriate functioning of the apparatus according to the invention it is important that the two peristaltic pumps P1 and P2 indeed have the same pumping capacity, thereby insuring that dialysate is supplied to and removed from the flow passage G through the dialyser at the same flow rate. The same amount of liquid which, by means of the dialysate is extracted from the blood flowing through the passage B, must then necessarily be tapped off through the tap outlet T. The flow rate of the tapped liquid may easily be measured by means of ordinary known flow gauges, or the liquid may be collected for measuring the total tapped amount during a given time interval.

The tapped liquid amount may also be automatically regulated by means of a further peristaltic pump U acting on the tap outlet T. This pump will then draw off liquid from the flow passage G through the tap outlet T at a certain preset rate. If this rate is greater than the extraction rate of the ultrafiltrate from the blood, the internal pressure in the through-flow passage G will decrease, and thereby the extracted amount of ultrafiltrate per time unit will increase until balance is established between extracted ultrafiltrate and tapped liquid amount. The opposite automatic adjustment will take place if the preset tapping rate of the pump U at a certain instant is greater than the amount of ultrafiltrate transferred per time unit from the blood to the dialysate.

As a subpressure usually prevails in the flow passage of dialysate between the two pump units, the peristaltic hose portion S adjacent the inlet of the pump unit P2 may presumably be compressed to a somewhat reduced effective flow cross-section, and in order to avoid that the two peristaltic pumps P1 and P2 thereby achieve different pumping capacities, the hose portion S may be designed as indicated in FIG. 2. As shown in this Figure, the hose portion S is provided with a sealed outer jacket K, the interior of which by means of apertures H communicates with the interior of the hose section. Thus, as with this design the same pressure prevails both inside and outside the hose portion S, this portion will not be compressed and consequently the pump unit P2 will be able to maintain full pumping capacity.

Figure 3B:
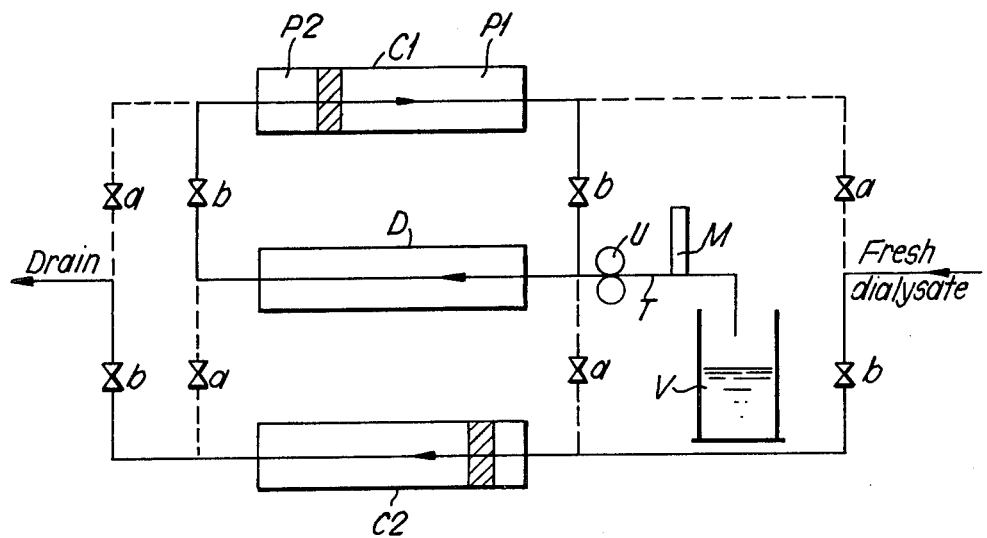

In FIGS. 3a and 3b there is schematically shown another embodiment of the apparatus according to the invention. In these Figures the corresponding components are designated with the same reference symbols as in FIGS. 1 and 2, and for the sake of clarity the flow circuit of the blood is not shown.

In this latter embodiment the pump units P1 and P2 comprise cylinder volumes on each side of the piston of a piston/cylinder unit C1 or C2. Thus, with the movement of the piston, the one side P1 of the piston functions as a pressure pump and is connected with the inlet side of the dialyser D, whereas the other side P2 of the piston functions as a suction pump and is connected with the outlet side of the dialyser. This function is shown for the piston/cylinder unit C2 in FIG. 3a and for the other piston/cylinder unit C1 in FIG. 3b.

It should, however, be understood that such a piston/cylinder unit must first be filled with dialysate before it can be effectively used in the manner indicated above. Thus, in the present embodiment the dialysis apparatus is provided with two piston/cylinder units C1 and C2, which are driven in synchronism and of which the one at any time received fresh dialysate and the other functions as pumping means for supplying the dialyser with previously received dialysate in the manner described above. Subsequent to each completed piston stroke in the two units C1 and C2, a controlled valve system is operatively actuated to interchange the indicated working functions of the units. This valve system comprises four valves identified as a in the Figures and four valves identified as b. These valves are controlled in such a manner that all valves a are open when the valves b are closed and vice versa. FIG. 3a illustrates the operative state in which the valves b in the flow conduits indicated by broken lines are closed while the other valves a are open. In this case dialysate will only flow in the flow circuits indicated by fully drawn lines in the Figure. With simultaneous and synchronous movement of the pistons in the two piston/cylinder units C1 and C2 to the left and to the right, respectively, fresh dialysate will be sucked into the cylinder volume on the right side of the piston of the unit C1, while previously used dialysate is pushed out of the cylinder volume on the left side of the piston, to be directed to a drain as shown in the Figure. At the same time, previously received fresh dialysate is pushed from the right side of the piston of the unit C2 into the dialyser D, in which the dialysate receives ultrafiltrate liquid from blood supplied to the dialyser. On the outlet side of the dialyser the mixture of ultrafiltrate and used dialysate is supplied to the left side of the piston in the unit C2. Since the closed circuit through the unit C2 and the dialyser D obviously cannot receive more liquid than it already contains, an amount of liquid corresponding to the received ultrafiltrate in the dialyser D will be pushed out through the tap outlet T. As shown in the Figures, this outlet is provided with a flowmeter M for gauging the tapping rate as well as a container V for measuring the total amount of tapped liquid during a predetermined time interval.

As illustrated in the FIGS. 3a and 3b, the tap output is also provided to a peristaltic pump U with the same automatic regulation function as described with reference to FIG. 1.

In the operative state illustrated in FIG. 3b, the working functions of the piston/cylinder units C1 and C2 are interchanged, as indicated by the fully drawn lines in the Figure. The valves a in the flow conduits shown in broken lines are closed in this case, whereas the valves b in the circuits shown in fully drawn lines, are open. The functioning of the apparatus is otherwise the same as described above with reference to FIG. 3a, and thus a more detailed description of FIG. 3b is believed not necessary.

In the embodiment illustrated in FIGS. 3a and 3b, the intended same pump capacity for the two pump units P1 and P2 is achieved with high accuracy and reliability, but on the other hand this embodiment is, due to the required valve system with a great number of controlled valves a and b, far more complex than the embodiment shown in FIG. 1. Furthermore, a careful cleansing and sterilisation of the piston/cylinder units C1 and C2 will be necessary after each dialysis treatment. The hose sets used in the peristaltic pumps of the embodiment of FIG. 1 are, however, rather inexpensive and may be discarded after use and replaced by new sterilized hoses before the next dialysis treatment.

With both the illustrated embodiments of the apparatus according to the invention an accurate and dependable indication of the extracted amount of ultrafiltrate from the blood of a patient, is readily achieved whether recirculating or through-running dialysate is used.

I claim:

1. Dialysis apparatus for regulated blood dialysis comprising a dialyzer having flow passages for blood and dialysate, respectively, separated by semipermeable barriers for transferring liquid from the blood to the dialysate, the blood and dialysate being driven through their respective flow passages by individually associated pumping means, the improvement wherein said pumping means for the dialysate comprise two peristaltic pumps mounted on a common shaft and having the same pumping capacity and being respectively disposed on the inlet and outlet sides of said flow passage for dialysate through the dialyzer, one of said pumps being connected between a dialysate source and the inlet of the flow passage for dialysate through the dialyzer, the other of said pumps being connected between the outlet of said flow passage and a dialysate discharge conduit, a peristaltically actuated hose section of the peristaltic pump on the outlet side of the dialysate flow passage being surrounded by a sealed jacket having an interior in open communication with the interior of said hose section, and a tap outlet connected with means for gauging the amount of tapped liquid being arranged in communication with said flow passage between said two pumps.

2. Dialysis apparatus as claimed in claim 1, wherein said tap outlet is provided with an adjustable pump for automatic regulation of the tapped amount of liquid and thereby the pressure in the flow passage for dialysate through the dialyser.

* * * * *